United States Patent [19]

Lapin et al.

[11] Patent Number: 4,845,265
[45] Date of Patent: Jul. 4, 1989

[54] POLYFUNCTIONAL VINYL ETHER TERMINATED ESTER OLIGOMERS

[75] Inventors: Stephen C. Lapin, Wauconda; Jorge M. Olivares, Chicago, both of Ill.

[73] Assignee: Allied-Signal Inc., Morristown, N.J.

[21] Appl. No.: 161,823

[22] Filed: Feb. 29, 1988

[51] Int. Cl.$^4$ .............................................. C07C 69/80
[52] U.S. Cl. ...................................... 560/84; 560/89; 560/91; 560/180; 560/193; 560/198; 526/320; 204/157.87; 204/157.9
[58] Field of Search ................. 560/84, 89, 91, 180, 560/193, 198; 204/157.87, 157.9; 522/108; 526/320

[56] References Cited

U.S. PATENT DOCUMENTS

| | | | |
|---|---|---|---|
| 3,935,173 | 1/1976 | Ogasawara | 522/104 |
| 4,093,601 | 6/1978 | Kuehn | 526/227 |
| 4,652,591 | 3/1987 | Londrigan | 521/172 |
| 4,654,379 | 3/1987 | Lapin | 521/15 |
| 4,749,807 | 6/1988 | Lapin | 560/91 |

Primary Examiner—John F. Niebling
Assistant Examiner—Isabelle Rodriguez
Attorney, Agent, or Firm—Harold N. Wells; Thomas K. McBride; Eugene I. Snyder

[57] ABSTRACT

There are described vinyl ether terminated ester oligomers which cure or polymerize particularly rapidly, especially by cationic polymerization which is radiation induced in the presence of an onium salt. The oligomeric units arise from the reaction of a polycarboxylic acid having at least three carboxylic acid groups with a diol, although esters with triols and higher polyhydric diols also are useful, especially where an extensively cross-linked product is desired. The carboxyl-terminated oligomeric esters are esterfied with vinyl ether terminated alcohols which can be thought of as the adducts of alkynes and diols.

18 Claims, No Drawings

POLYFUNCTIONAL VINYL ETHER TERMINATED ESTER OLIGOMERS

BACKGROUND OF THE INVENTION

Vinyl ethers are extremely reactive monomers which are known to undergo polymerization by a cationic mechanism and are useful in applications which require a high speed curing of a resin formulation. The vinyl ethers react much faster than the epoxy resins and therefore may be used for printing inks, coatings, elastomers, foams, and other types of products dependent upon the ability of the resin to cure at a rate which is consistent with other processing steps. A disadvantage attendant to the use of vinyl ethers is that their commercial availability is relatively limited. In general, the available vinyl ethers are low molecular weight monofunctional or difunctional monomers, whereas in most commercial applications higher molecular weight oligomeric materials are preferred.

The present invention discloses vinyl ether terminated esters. As will be seen, the structure of such esters is susceptible to wide variations with a minimum change in the reactants. This flexibility permits facile variation in the properties and characteristics of the vinyl ether terminated ester oligomers as well as comparable variations in the resulting cured resins. Where the oligomer contains more than one vinyl ether group the cured resins are extensively cross-linked, very high molecular weight polymers. The polymers are thermosetting materials with a wide range of properties depending upon the structure of the oligomeric precursor. Although the vinyl ether terminated esters of this invention have been designed to fill the need for radiation curable coatings, they may have a much broader use. In particular, the esters of our invention are readily polymerized by means other than radiation curing, and the resulting polymers are meant to be subsumed in our invention.

SUMMARY OF THE INVENTION

The purpose of our invention is to provide vinyl ethers which are readily and economically synthesized and with structures whose permutations are large in number but each of which as easily made, with at least most of the resulting materials able to be radiation cured to afford polymer coatings. An embodiment is the class of polyfunctional vinyl ether terminated oligomeric esters where the acid portion of the ester is a polycarboxylic acid which is at least a tricarboxylic acid. In a more specific embodiment the alcohol portion of the ester is a vinyl ether which can be viewed as the adduct of an acetylenic compound and an ethylene or propylene glycol or a bis(hydroxyalkyl)cycloalkane. In another embodiment the alcohol portion of the ester is a vinyl ether which may be viewed as the adduct of an acetylenic compound and a poly(ethylene) or poly(propylene) glycol. In a further embodiment the acetylenic compound is terminal acetylene. In a still further embodiment the acid portion of the ester is a tricarboxylic acid. In yet another specific embodiment a glycol is used as a chain extender for the oligomeric ester. Other embodiments will become apparent from the detailed discussion within.

DESCRIPTION OF THE INVENTION

The invention to be described in greater detail within is a class of compounds with a broad spectrum of molecular weight but which is characterized by the presence of one or more terminal vinyl ether moieties and which are esters of polycarboxylic acids. One of the reactants used in making the products of our invention is, or may be viewed as, an adduct of an acetylenic compound (an alkyne) with a diol, the resulting material being a vinyl ether terminated alcohol. For simplicity, a generic diol, HOXOH, will be used in this section as representative of diols generally in order to represent one means of preparing the vinyl ether terminated alcohol under discussion, namely,

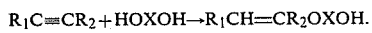

If the vinyl ether terminated alcohol is prepared as an adduct, reaction conditions usually are so chosen as to form the monoadduct either to the virtual exclusion of the diadduct or, more likely, in large preponderance relative to the diadduct. the monoadduct can be isolated and used in a purified form, but more often the entire reaction mixture is used as the alcoholic reactant in ester formation with carboxylic acids, where the unreacted glycol (or diol) has the important function of a chain extender.

The vinyl ether terminated alcohol is then reacted with a polycarboxylic acid. In reality, reaction of the alcohol and carboxylic acid is too slow or too incomplete for commercial preparation, and the alcohol is reacted with some activated derivative of a carboxylic acid, such as an acid chloride or anhydride. But for simplicity and clarity of exposition we shall continue to refer to reaction with a carboxylic acid. In the case where the acid is a tricarboxylic acid the reaction may be represented as,

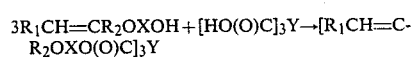

The above reaction is most accurate where the alcoholic reactant is solely

and in the more usual cases where the alcoholic reactant is a mixture containing unreacted glycol, or where a second glycol is added to the vinyl ether terminated alcohol, the product is a mixture of oligomeric esters.

Such oligomeric esters, which arise in a more-or-less typical condensation reaction of a polyfunctional carboxylic acid acid and glycol, can be envisioned as arising from multiple consecutive esterification reactions where the polycarboxylic acids first react with the glycol to form oligomeric polycarboxylic acids. The latter then can be end-capped by esterification with a vinyl ether terminated alcohol to afford the oligomeric product. The oligomeric esters need not arise from the precise reaction sequence described above, for other sequences can lead to the same oligomeric esters. It will be readily appreciated that because of the polyfunctionality of the carboxylic acids used, the products will be a complex mixture differing in molecular weight, in relative number of vinyl ether groups, and so forth.

The vinyl ether terminated alcohols which are used in preparing the oligomeric esters of this invention have a structure corresponding to the adduct of an alkyne and a diol. In this application the terms "diol" and "glycol" are used interchangeably and meant to be equivalent. It must be emphasized that although some of the vinyl ether terminated alcohols of this invention may in fact be made by the addition of diols to alkynes, the vinyl ether terminated alcohols herein also can be made in other ways, and the alternative routes to such alcohols are often preferred. The alkyne has the generic formula $R_1C\equiv CR_2$, and the diol has the generic formula $X(OH)_2$. The generic formula of the vinyl ether terminated alcohols of our invention is then $R_1CH=CR_2OXOH$.

The groupings $R_1$ and $R_2$ are independently selected from the group consisting of hydrogen and lower alkyl moieties containing from 1 to 10 carbon atoms, although those with from 1 to about 4 carbon atoms are favored. It is preferable that both $R_1$ and $R_2$ are not alkyl moieties, for in the case where both are lower alkyl groups this causes a reduction in polymerization rate of the oligomers of our invention to a point where the polymerization rate is undesirable. Where $R_1$ is an alkyl moiety it is preferred that $R_2$ be hydrogen, and conversely; those cases where $R_2$ is hydrogen and $R_1$ an alkyl of 1 to 4 carbons are quite desirable. In a preferred embodiment $R_1(R_2)$ is a methyl group and $R_2(R_1)$ is hydrogen. In a still more preferred embodiment both $R_1$ and $R_2$ are hydrogen.

In the vinyl ether alcohol fragment the grouping —OXOH arises from, or can be thought of as arising from, a diol of structure $X(OH)_2$. Among the diols HOXOH supplying the necessary grouping in the vinyl ether alcohol fragment one important class consists of alkylene glycols, $HO(C_nH_{2n})OH$, where n is an integer from 2 to about 10. The linear alkylene glycols, $HO(CH_2)_nOH$, (polymethylenediols), where n is an integer from 2 to about 10, are particularly useful, especially where n is from 2 to about 6. Illustrative of the members of this group are such diols as ethylene glycol, 1,3-propylene glycol, 1,4-butanediol, 1,5-pentanediol, 1,6-hexanediol, 1,7-heptanediol, 1,8-octanediol, 1,9-nonanediol, and 1,10-decanediol (decamethylene glycol).

The nonlinear or branched alkylene diols also may be used to supply the fragment —OXOH, where such glycols contain from 3 up to about 10 carbon atoms. Examples include 1,2-propylene glycol, 2,3-butanediol, 2,3-dimethyl-2,3-butanediol, 2,3-dimethyl-1,4-butanediol, etc.

Another class of diols useful as a source of the grouping —OXOH are the polyalkyleneoxy glycols, especially poly(ethyleneoxy) glycols, $[—CH_2CH_2O—]_m$, and poly(propyleneoxy) glycols, $[—CH(CH_3)CH_2O—]_m$, where m is an integer from 1 up through about 50, although more usually m is an integer from 1 up to about 10, and most preferably from 1 up t0 about 5. Examples of the glycols in this branch of the invention include diethylene glycol, triethylene glycol, tetraethylene glycol, pentaethylene glycol, hexaethylene glycol, etc., along with the analogs of the propyleneoxy glycols.

Yet another class of diols used in the practice of this invention are bis(hydroxyalkyl)cycloalkanes whose formula is $(HO(CH_2)_n)_2R$. It is to be noted that in all cases the hydroxyl moiety is a primary hydroxyl, i.e., it is located at the end of the alkylene chain. In the diols of this branch of our invention n is an integer from 1 through about 6, preferably from 1 to 3, and the member where n=1 is highly preferred. R is a divalent radical whose parent is a cyclopentane, cyclohexane, cycloheptane, or cyclooctane, with the cyclohexanes being favored because of their relative availability.

Examples of the aforementioned diols include bis(hydroxymethyl)cyclopentane, bis(2-hydroxyethyl)cyclopentane, bis(3-hydroxypropyl)cyclopentane, bis(4-hydroxybutyl)cyclopentane, bis(5-hydroxypentyl)cyclopentane, bis(6-hydroxyhexyl)cyclopentane, bis(hydroxymethyl)cyclohexane, bis(2-hydroxyethyl)cyclohexane, bis(3-hydroxypropyl)cyclohexane, bix(4-hydroxybutyl)cyclohexane, bis(5-hydroxypentyl)cyclohexane, bis(6-hydroxyhexyl)cyclohexane, and the cycloheptane and cyclooctane analogs of the foregoing diols.

As regards the orientation of the hydroxy alkyl groups, the preferred members are the 1,3-bis(hydroxyalkyl)cyclopentanes and the 1,4-bis(hydroyalkyl)cyclohexanes, -cycloheptanes, and -cyclooctanes. Diols substituted at positions different from those specified above may be used in the practice of this invention, but not necessarily with equivalent results. The bis(hydroxymethyl)cyclohexanes are a highly preferred dioal used in the practice of this invention as they are readily available from the reduction of the corresponding phthalic acids, and among these 1,4-bis(hydroxymethyl)cyclohexane is greatly favored.

The vinyl ether terminated alcohol is then reacted with a polycarboxylic acid which is at least a tricarboxylic acid to afford a vinyl ether terminated ester. There are four quite distinct variants here, three of which utilize diol $Z(OH)_2$ as a reactant. In one variant the purified vinyl ether terminated alcohol alone is reacted with the acid. In a second variant a mixture of the vinyl ether terminated alcohol and the unreacted diol from which it was made, or could be thought of as being made, is reacted with the acid. In this variant the diol, $Z(OH0_2$, acts as a chain extender by esterifying the polycarboxylic acid to give an oligomeric ester where $X=Z$. In another variant a mixture of the vinyl ether terminated alcohol and a second diol, $Z(OH)_2$, is reacted with the acid. Again the diol acts as a chain extender via ester formation with the carboxylic acid, but in this case X and Z are different. Finally, in a fourth variant a mixture of vinyl ether terminated alcohol, unreacted diol from which it was made or could be thought to be made, and a second, unrelated diol is reacted with the polycarboxylic acid. As in the cases above, the unreacted diols react with the carboxylic acid to afford oligomeric esters, and in this variant some of Z are different from X and some are the same.

The components of the alcohol mixture reacting with the carboxylic acid are $R_1CH=CR_2OX(OH)$ (component A), $X(OH)_2$ (component B), and $Z(OH)_2$ (component C), where $Z(OH)_2$ is selected from the same group as $X(OH)_2$, but merely denotes a different member of that group. In the reactant alcohol mixture the molar proportions of $(B+C)/A$ may be between 0 and about 100. Where the ratio is 0 there is no free diol which may be a common and desirable case, but generally the alcohol mixture will contain not only a vinyl ether terminated alcohol but also some diol. In the preferred case the ratio above is between about 0 and about 5.

As alluded to above, the reaction between alcohols and carboxylic acids to give the esters of this invention is too slow and occasionally too incomplete to be a practical method of preparation, and activated derivatives of carboxylic acids are in fact used as reactants. Among such derivatives the acid chlorides and anhydrides are most frequently employed, and the following description refers to the carboxylic acids which are parents of the activated acid derivatives used to prepare our oligomeric esters.

Turning to the polycarboxylic acids which may be used, or which are parents of activated derivatives which may be used in the practice of this invention, it has previously been mentioned that at least tricarboxylic acids are necessary. Among the tricarboxylic acids which represent the acid portion of the vinyl ether terminated esters of this invention may be mentioned the benzenetricarboxylic acids, especially 1,3,5-benzenetricarboxylic acid (trimesic acid), 1,2,4-benzenetricarboxylic acid (trimellitic acid), their reduced hexahydro counterparts, and citric acid. Among the tetracarboxylic acids may be mentioned the benzenetetracarboxylic acids, especially 1,2,4,5-benzenetetracarboxylic acid) pyromellitic acid), 3,3',4,4'-benzophenonetetracarboxylic acid, 1,4,5,8-naphthalenetetracarboxylic acid, their reduced hexahydro counterparts, and bicyclo [2.2.1]heptane-2,3,5,6-tetracarboxylic acid.

Where the alcohol mixture contains 1 or more diols there are 3 subvariants possible. In all cases the alcohol mixture contains at least one vinyl ether terminated alcohol, and the subvariants are the cases where the mixture also contains the diol containing the structural grouping found in the ether, an unrelated diol, or a mixture of the above. In either of these cases, the ratio of molar proportions of diol to vinyl ether terminated alcohol is up to about 100, and preferably is from about 0 to about 5.

As previously stated, the structure of the products of this invention is capable of enormous permutation. For example, each of the hydroxyls of the diol can react with a different oligomeric ester subunit arising from the reaction of a polycarboxylic acid and a diol. Also, in any subunit of the oligomeric ester a diol may react intermolecularly with various carboxyl groups to afford extensively cross-linked subunits. An important characteristic of our invention is that in all cases there are essentially no free hydroxyl groups arising from the diol in the final product. That is, less than about 5% of the initial hydroxyl groups of the diols remain unreacted. This is desirable to afford a polymer with good characteristics.

The vinyl ether terminated oligomeric esters of this invention may be cured or polymerized by any method known in the art. For example, the resins may be radiation cured, as for example by being subjected to an electron beam of an energy in the range from about 50 up to perhaps 500 KeV with a dosage from about 0.1 to about 10.0 Mrads. Electron beam curing may be performed advantageously in the presence of an iodonium or a sulfonium salt to afford high speed cationic polymerization. Ultraviolet curing in the presence of an onium salt also may be executed to afford cationic polymerization. Other means include thermal curing in the presence of a Lewis acid, such as boron trifluoride, or in the presence of a strong acid such as p-toluenesulfonic acid and trifluoromethylsulfonic acid. All these methods of polymerization are well known to those versed in the art and need not be elaborated upon further.

The high crosslinking density of the products of our invention affords polymeric coatings with excellent solvent resistance. Increasing crosslinking density often is accompanied by harder, less flexible coatings with lower elongation and impact resistance, and where these properties are not desired crosslink density may be reduced by diluting the products of our invention with, for example, vinyl ethers of lower crosslinking density, such as vinyl ethers of various monofunctional and difunctional alcohols. Monofunctional vinyl ethers are best for reducing crosslink density, and illustrative of the readily available vinyl ethers are isooctyl vinyl ether, decyl vinyl ether, hexadecyl vinyl ether, octadecyl vinyl ether, n-butyl vinyl ether, and isobutyl vinyl ether. In general, the vinyl ether of any alkanol or cycloalkanol may be used in the practice of this aspect of my invention. Among the vinyl ethers of difunctional alcohols may be mentioned triethylene glycol divinyl ether, diethylene glycol divinyl ether, 1,4-cyclohexane dimethanol divinyl ether, and 1,6-hexanediol divinyl ether as exemplary of this class.

The following examples are only illustrative of our invention which is not to be limited thereto or circumscribed thereby in any way.

EXAMPLE 1

Synthesis of Oligomeric Ester Based on 1,3,5-Benzenetricarboxylic (Trimesic) Acid.

Triethyleneglycol monovinyl ether, (TEGMVE, 20 g, 0.114 moles), triethylamine (14 g) and dimethylaminopyridine (0.2 g) were combined with 150 mL of anhydrous ether in 250 mL round bottom flask fit with an addition funnel, condenser and stirrer. The addition funnel was charged with trimesoyl chloride (10.0 g, 0.038 mol) in 70 mL of ether. The acid chloride solution was added dropwise over a 40 min. period. Solid triethylamine hydrochloride precipitated from the reaction mixture. The mixture was filtered and then washed two times with 300 mL of 2% $H_3PO_4$ followed by 5% $NaHCO_3$ and then water. The ether layer was dried over $Na_2SO_4$ and was then concentrated in a vacuum to afford 16.22 g (60% yield) of a clear, light yellow liquid, A. The HNMR was consistent with the expected product.

The procedure was repeated using 1,4-butanediol monovinyl ether, BDMVE, in place of TEGMVE to produce an analogous ester B.

EXAMPLE 2

Radiation Curing

Samples to be irradiated were combined with a triarylsulfonium salt (General Electric UVE-1016, 2 weight percent) and were coated onto either Bonderite-40 treated steel test panels (Parker Chemical) or polyethylene coated paper board. An excess of the sample was placed at one end of the substrate and a #6 wire would rod was drawn across the substrate with even pressure pushing excess material off the edge. This method produced coatings with a thickness of 6 to 12 μm.

An RPC model QC-1202 processor was used for UV curing. The unit was equipped with two 12 inch medium pressure mercury arc lamps and a variable speed conveyor (50 to 500 ft/min). Only one lamp was used at a time in the testing (operated at 200 watts/in).

An Energy Sciences Electrocurtain model CB-150 equipped with a 15 cm linear cathode was used for EB curing. Electron energies of 160 KeV were employed. Samples were placed in an aluminum tray on a variable speed conveyor (20–235 ft/min) within the CB-150 unit. Irradiation occurred in a nitrogen atmosphere.

The coatings were evaluated within one hour after irradiation. The coatings were examined for solvent resistance using methyl ethyl ketone. The number of double rubs necessary to break through the coating was recorded. Reverse impact was measured on the steel panels using a Gardner impact tester according to ASTM Method D2794. The coating elongation was measured by bending the coated steel panel over a conical mandrel according to ASTM Method D522. Adhesion was measured according to ASTM D3359 using Scotch 610 adhesive tape. Pencil hardness was measured according to ASTM D3363.

TABLE 1

Properties of UV Cured[a] Coatings

| VEE | Max. Conveyor Speed for Tack-free Cure (ft/min) | MEK Double Runs[c] | Adhesion[c] PE/Treated Steel (%) | Pencil Hardness[c] | Elongation[c] (%) | Reverse Impact[c] (in-lbs) |
|---|---|---|---|---|---|---|
| A | >500[b] | >200 | 100/0 | 3H | 18 | 50 |
| B | >500[b] | >200 | 100/0 | 2H | 9 | 4 |

[a]One 200 watt/in. medium pressure mercury arc lamp.
[b]Maximum speed of curing unit.
[c]After curing at 250 ft/min.

TABLE 2

Properties of EB Cured Coatings

| VEE | Min. EB Dose for Tack-free Cure (Mrads) | MEK* Double Rubs | Adhesion* PE/Treeated Steel (%) | Pencil* Hardness | Elongation* (%) | Reverse Impact (in-lbs) |
|---|---|---|---|---|---|---|
| A | 0.50 | 70 | 40/0 | 2H | 20 | 30 |
| B | 0.75 | >200 | 100/4 | 3H | 8 | 4 |

*After EB curing at 4.0 Mrads.

EXAMPLE 3

Preparation of an Oligomeric Multifunctional Vinyl Ether Ester

A higher molecular weight material may be prepared by including a difunctional alcohol in the reaction mixture. Thus, diethylene glycol (10.5 g, 0.1 mol) and diethylene glycol monovinyl ether (DEGMVE, 52.4 g, 0.4 mol) may be combined with triethylamine (60 g) and dimethylaminopyridine (0.8 g) along with 250 mL of anhydrous ether in a one liter round bottom flask fit with an addition funnel, condenser and stirrer. The addition funnel may be changed with trimesoyl chloride (53.1 g, 0.2 mol) in 200 mL of ether. The acid chloride solution may be added dropwise over a 1.0 hour period. When reaction is complete, the mixture is filtered and then washed two times with 1.0 L of 2% $H_3PO_4$ followed by 5% $NaHCO_3$ and then water. The products may be obtained after evaporating the ether in a vacuum. The product is a mixture of various molecular weight oligomers, and may be combined with an appropriate onium salt catalyst and cured by UV or EB irradiation.

What is claimed is:

1. A vinyl ether terminated oligomeric ester containing fewer than 5% unreacted alcoholic hydroxyl groups which is the esterification reaction product of a vinyl ether terminated alcohol of the formula $R_1CH=CR_2OXOH$, or a mixture of alcohols containing 1 molar proportion of a vinyl ether terminated alcohol of the aforesaid formula and from 0 to about 100 molar proportions of at least one diol of formula $Z(OH)_2$, with a sufficient amount of a polycarboxylic acid having at least three carboxyl moieties such that there are essentially no free alcoholic hydroxyl groups in the resulting ester, where:

$R_1$ and $R_2$ are independently selected from the group consisting of hydrogen and lower alkyl moieties containing up to about 10 carbon atoms;

$X(OH)_2$ is selected from a group whose members are, an alkylene diol of the formula $HO(C_nH_{2n})OH$, where n is an integer from 2 to about 10; or a poly(ethyleneoxy) or poly(propyleneoxy) glycol, $HO-[-CH_2CH_2O]_m-H$ or $HO-[-CH(CH_3)CH_2O]_m-H$, respectively, where m in an integer from 1 to about 50; or a bis(hydroxyalkyl)cycloalkane of formula $[HO(CH_2)_n]_2R_3$ where n is an integer from 1 to about 6, and $R_3$ is a divalent radical whose parent is a saturated cyclic hydrocarbon of ring size 5 to 8 carbons; and $Z(OH)_2$ is a diol selected from the same preceding group containing $X(OH)_2$, or any combination thereof.

2. The vinyl ether terminated oligomer of claim 1 where $R_2$ is hydrogen and $R_1$ is an alkyl group of 1 to about 4 carbon atoms.

3. The vinyl ether terminated oligomer of claim 1 where $R_1$ and $R_2$ are hydrogen.

4. The vinyl ether terminated oligomer of claim 1 where $R_1$ is hydrogen and $R_2$ is methyl, or $R_1$ is the methyl and $R_2$ is hydrogen.

5. The vinyl ether terminated oligomer of claim 1 where HOXOH is a linear polymethylenediol, $HO(CH_2)_nOH$, where n is an integer from 2 to about 10.

6. The vinyl terminated oligomer of claim 5 where the polymethylenediol has from 2 to about 6 carbon atoms.

7. The vinyl ether terminated oligomer of claim 1 where HOXOH is a poly(ethleneoxy) or poly(propyleneoxy) glycol where m is an integer from 1 through about 10.

8. The vinyl ether terminated oligomer of claim 7 where m is an integer from 1 to about 5.

9. The vinyl ether terminated oligomer of claim 1 where the polycarboxylic acid is a tricarboxylic acid.

10. The vinyl ether terminated oligomer of claim 1 where the polycarboxylic acid is a tetracarboxylic acid.

11. The vinyl ether terminated oligomer of claim 9 where the acid is 1,3,5-benzenetricarboxylic acid.

12. The vinyl ether terminated oligomer of claim 10 where the acid is 1,2,4,5-benzenetetracarboxylic acid.

13. The vinyl ether terminated oligomer of claim 1 where HOXOH is a bis(hydroxymethyl)cyclopentane, -cyclohexane, -cycloheptane, or -cyclooctane.

14. The vinyl ether terminated oligomer of claim 13 where HOXOH is a bix(hydroxymethyl)cyclohexane.

15. The vinyl ether terminated oligomer of claim 14 where HOXOH is 1,4-bis(hydroxymethyl)cyclohexane.

16. The polymeric product resulting from polymerizing the vinyl ether terminated oligomer of claim 1.

17. The polymeric product of claim 16 further characterized in that polymerizing is effected by radiation curing.

18. The polymeric product of claim 16 further characterized in that the vinyl ether terminated oligomer contains a divinyl ether.

* * * * *

UNITED STATES PATENT AND TRADEMARK OFFICE
CERTIFICATE OF CORRECTION

PATENT NO. : 4,845,265
DATED : July 4, 1989
INVENTOR(S) : Lapin et al.

It is certified that error appears in the above-identified patent and that said Letters Patent is hereby corrected as shown below:

```
Column 2, line 18:  ".the monoadduct" should read
                    --. The monoadduct--;
          line 49:  "acid acid" should read --acid--.
Column 3, line 52:  "tO" should read --to--.
Column 4, line 19:  "dioal" should read --diol--;
          line 34:  "Z(OHO2," should read --Z(OH)2,--.
Column 5, line 16:  "acid) pyromellitic acid)," should read
                    --acid (pyromellitic acid),--.
Column 6, line 50:  "would" should read --wound--.
Column 7, line 42:  "changed" should read --charged--;
Column 8, line 42:  delete "the" after --R1 is--;
          line 68:  "bix" should read --bis--.
```

Signed and Sealed this

Fifteenth Day of May, 1990

Attest:

HARRY F. MANBECK, JR.

Attesting Officer    Commissioner of Patents and Trademarks